US012629190B2

(12) United States Patent
Day et al.

(10) Patent No.: US 12,629,190 B2
(45) Date of Patent: May 19, 2026

(54) INTERNAL BEAM PLATES AND ASSOCIATED INSTRUMENTATION FOR PERFORMING SURGICAL METHODS

(71) Applicant: ARTHREX, INC., Naples, FL (US)

(72) Inventors: Zachary Day, Naples, FL (US); Chris Powell, Naples, FL (US); Mihaela Morar, Naples, FL (US); Carl Hasselman, Oakmont, PA (US)

(73) Assignee: ARTHREX, INC., Naples, FL (US)

( * ) Notice: Subject to any disclaimer, the term of this patent is extended or adjusted under 35 U.S.C. 154(b) by 422 days.

(21) Appl. No.: 17/195,830

(22) Filed: Mar. 9, 2021

(65) Prior Publication Data

US 2021/0282823 A1     Sep. 16, 2021

Related U.S. Application Data

(60) Provisional application No. 62/989,231, filed on Mar. 13, 2020, provisional application No. 62/987,567, filed on Mar. 10, 2020.

(51) Int. Cl.
*A61B 17/80* (2006.01)
*A61B 17/17* (2006.01)
(Continued)

(52) U.S. Cl.
CPC ........ *A61B 17/809* (2013.01); *A61B 17/1728* (2013.01); *A61B 2017/564* (2013.01); *A61B 17/848* (2013.01); *A61B 2090/034* (2016.02); *A61F 2002/30172* (2013.01); *A61F 2002/30622* (2013.01); *A61F 2002/30884* (2013.01)

(58) Field of Classification Search
CPC .............. A61B 17/8061; A61B 17/809; A61B 17/8095; A61B 2017/564
See application file for complete search history.

(56) References Cited

U.S. PATENT DOCUMENTS

| | | | | | |
|---|---|---|---|---|---|
| 5,620,448 | A | * | 4/1997 | Puddu | A61B 17/88 |
| | | | | | 606/83 |
| 6,852,113 | B2 | * | 2/2005 | Nathanson | A61B 17/8095 |
| | | | | | 606/71 |

(Continued)

FOREIGN PATENT DOCUMENTS

| | | |
|---|---|---|
| CN | 108567465 A | 9/2018 |
| CN | 106236238 B | 7/2019 |
| CN | 110251192 A | 9/2019 |

*Primary Examiner* — Anu Ramana
(74) *Attorney, Agent, or Firm* — Carlson, Gaskey & Olds, P.C.

(57) ABSTRACT

Internal beam plates and associated instrumentation may be utilized for performing arthrodesis procedures, bone fracture procedures, osteotomy procedures, etc. Exemplary surgical methods that may be performed using the internal beam plates and associated instrumentation include, but are not limited to, lapidus bunionectomy procedures, metatarsophalangeal (MTP) procedures, chevron procedures, fracture repair procedures, etc. The exemplary internal beam plates incorporate an integral beam that is configured to increase strength and stiffness across a fusion site. The exemplary cutting/prep guides are configured to allow surgeons to reduce, prepare, and cut bones for receiving the beam of the internal beam plate using one or more guides.

16 Claims, 15 Drawing Sheets

(51) Int. Cl.

| | |
|---|---|
| A61B 17/56 | (2006.01) |
| A61B 17/84 | (2006.01) |
| A61B 90/00 | (2016.01) |
| A61F 2/30 | (2006.01) |

(56) References Cited

U.S. PATENT DOCUMENTS

| | | | | |
|---|---|---|---|---|
| 7,931,680 | B2 | 4/2011 | Myerson et al. | |
| 8,066,777 | B2 | 11/2011 | Palmer et al. | |
| 8,591,553 | B2 | 11/2013 | Eisermann et al. | |
| 8,784,457 | B2 * | 7/2014 | Graham | A61B 17/809 |
| | | | | 606/286 |
| 8,998,903 | B2 | 4/2015 | Price et al. | |
| 9,144,443 | B2 * | 9/2015 | Leither | A61B 17/8085 |
| 9,259,251 | B2 * | 2/2016 | Kay | A61B 17/8057 |
| 9,545,278 | B2 * | 1/2017 | Ducharme | A61B 17/8061 |
| 9,861,404 | B2 * | 1/2018 | Reiley | A61B 17/80 |
| 9,936,984 | B2 | 4/2018 | Blain | |
| 9,949,773 | B2 * | 4/2018 | Dacosta | A61B 17/80 |
| 9,987,024 | B2 | 6/2018 | Frey et al. | |
| 10,130,487 | B2 | 11/2018 | Faulhaber | |
| 10,285,689 | B2 | 5/2019 | Finley et al. | |
| 10,433,888 | B2 | 10/2019 | Hollis et al. | |
| 10,524,808 | B1 | 1/2020 | Hissong et al. | |
| 10,561,426 | B1 | 2/2020 | Dayton et al. | |
| 11,154,342 | B2 * | 10/2021 | Wahl | A61B 17/8095 |
| 11,464,554 | B2 * | 10/2022 | Felder | A61B 17/8047 |
| 11,622,801 | B2 * | 4/2023 | Robichaud | A61B 34/10 |
| | | | | 606/88 |
| 2003/0199875 | A1 * | 10/2003 | Mingozzi | A61B 17/8095 |
| | | | | 606/297 |
| 2004/0093081 | A1 * | 5/2004 | Nilsson | A61F 2/30756 |
| | | | | 623/13.18 |
| 2006/0015103 | A1 | 1/2006 | Burke | |
| 2006/0173459 | A1 * | 8/2006 | Kay | A61B 17/8061 |
| | | | | 606/280 |
| 2009/0222047 | A1 * | 9/2009 | Graham | A61B 17/8061 |
| | | | | 606/280 |
| 2011/0087229 | A1 * | 4/2011 | Kubiak | A61B 17/1728 |
| | | | | 606/70 |
| 2011/0087295 | A1 * | 4/2011 | Kubiak | A61B 17/8014 |
| | | | | 606/70 |
| 2013/0018424 | A1 | 1/2013 | Subik | |
| 2013/0123923 | A1 * | 5/2013 | Pavlov | A61F 2/4455 |
| | | | | 606/279 |
| 2016/0100848 | A1 | 4/2016 | Lin et al. | |
| 2017/0164990 | A1 | 6/2017 | Weiner et al. | |
| 2018/0110530 | A1 | 4/2018 | Wagner et al. | |
| 2018/0125504 | A1 | 5/2018 | Dayton et al. | |
| 2018/0193034 | A1 | 7/2018 | Sikora et al. | |

* cited by examiner

INTERNAL BEAM PLATES AND ASSOCIATED INSTRUMENTATION FOR PERFORMING SURGICAL METHODS

CROSS-REFERENCE TO RELATED APPLICATIONS

This disclosure claims priority to U.S. Provisional Application No. 62/987,567, filed on Mar. 10, 2020, and U.S. Provisional Application No. 62/989,231, filed on Mar. 13, 2020, the entire disclosures of which are hereby incorporated by reference.

BACKGROUND

This disclosure relates to the field of surgery, and more particularly to internal beam bone plates and associated instrumentation and surgical methods.

A variety of surgical devices are used to treat bone abnormalities, such as bunions and fractures. For example, bone plates are commonly employed during orthopedic surgeries to stabilize, fuse, and/or align bones or bone fragments in order to restore functionality to a joint.

SUMMARY

This disclosure is directed to internal beam plates and associated instrumentation for performing arthrodesis procedures (i.e., bone fusion procedures), bone fracture procedures, osteotomy procedures, etc.

An exemplary internal beam plate may include, inter alia, a plate body and a beam. The plate body extends along a longitudinal axis between a first portion and a second portion and includes a bone contacting surface and an outer surface opposed to the bone contacting surface. The beam protrudes outwardly from the bone contacting surface.

An exemplary cutting/prep guide may include, inter alia, a guide body extending along a longitudinal centerline axis between a first section and a second section and including a bone contacting surface and an outer surface opposed to the bone contacting surface. A longitudinal cutting slot is formed through the guide body and extends along the longitudinal centerline axis. A vertical cutting slot is formed through the guide body and intersects the longitudinal cutting slot. A vertical guiding slot is formed through the guide body and extends in parallel with the vertical cutting slot but without intersecting the longitudinal cutting slot.

An exemplary surgical method may include, inter alia, fixating a cutting/prep guide to a first bone, inserting a first K-wire through a vertical guiding slot of the cutting/prep guide and into a second bone, moving the first K-wire within the vertical guiding slot to re-position a second bone relative to the first bone, inserting a surgical cutting device through a longitudinal cutting slot of the cutting/prep guide, preparing a slot within the first and second bones, removing the cutting/prep guide, positioning a beam of an internal beam plate within the prepared slot, and fixating the internal beam plate to both the first bone and the second bone.

Another exemplary surgical method may utilize multiple cutting/prep guides for preparing a bone or bones for receiving a beam of an internal beam plate.

DETAILED DESCRIPTION

Figure 1:
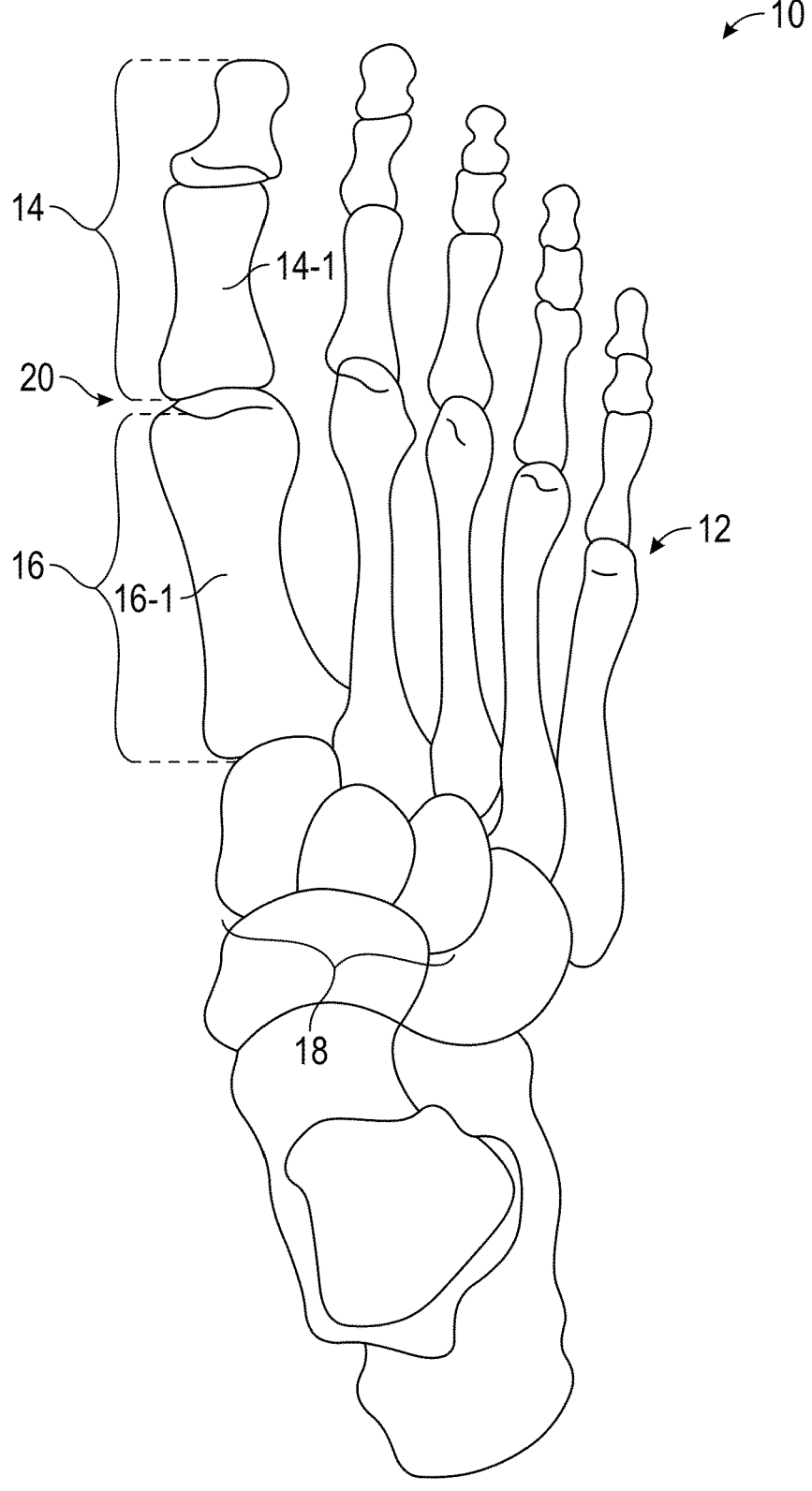
FIG. 1 illustrates a foot of the human musculoskeletal system. The foot includes a bone abnormality.
Figure 2:
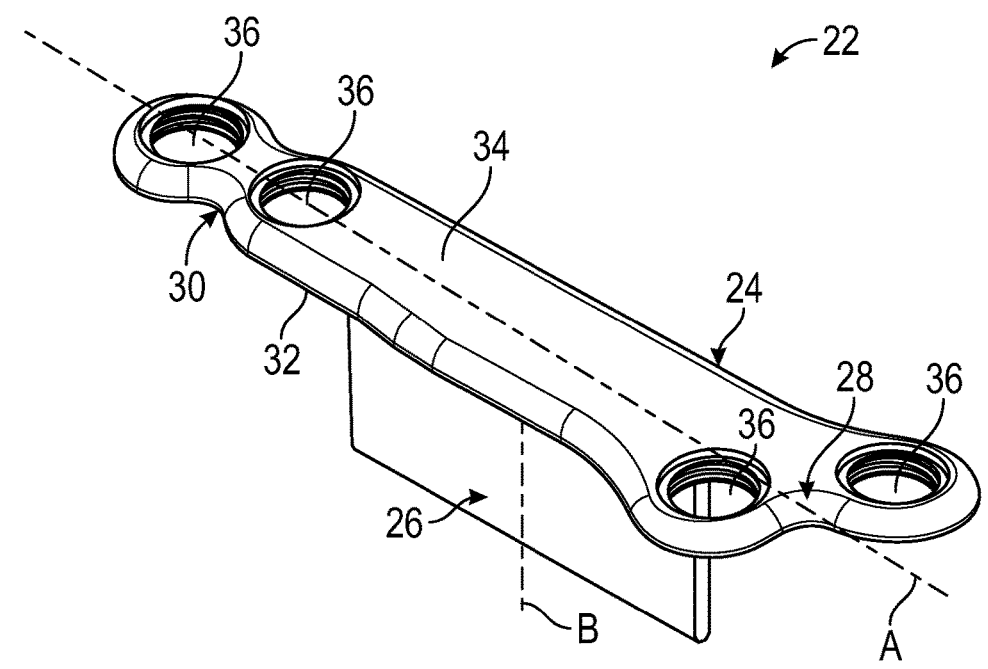
FIG. 2 is a perspective view of an exemplary internal beam plate for correcting a bone abnormality according to an embodiment of this disclosure.
Figure 3:
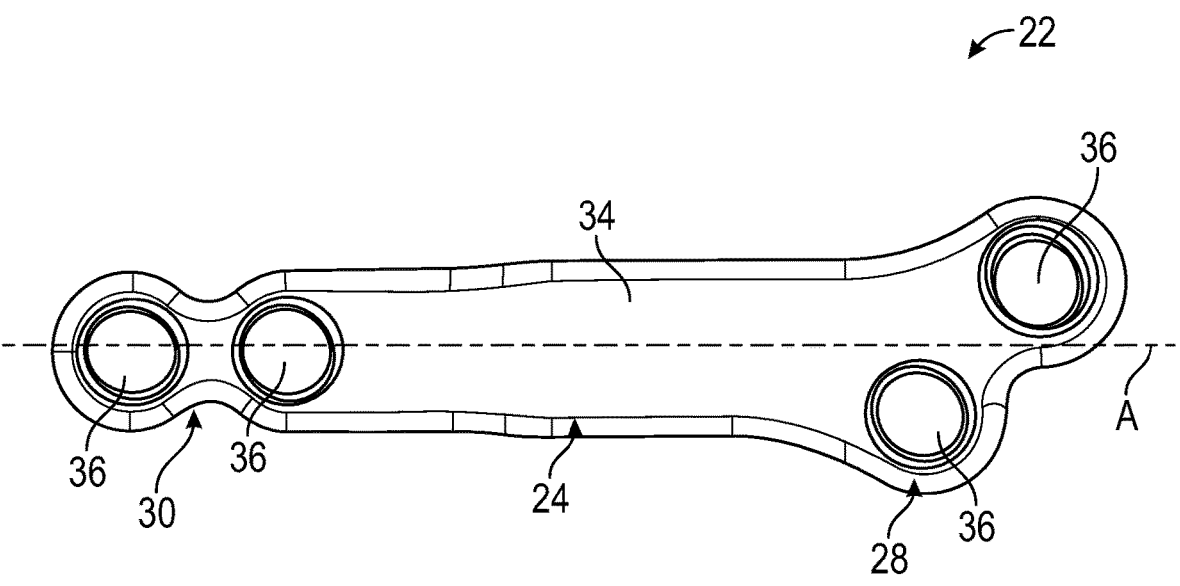
FIG. 3 is a top view of the internal beam plate of FIG. 2.
Figure 4:
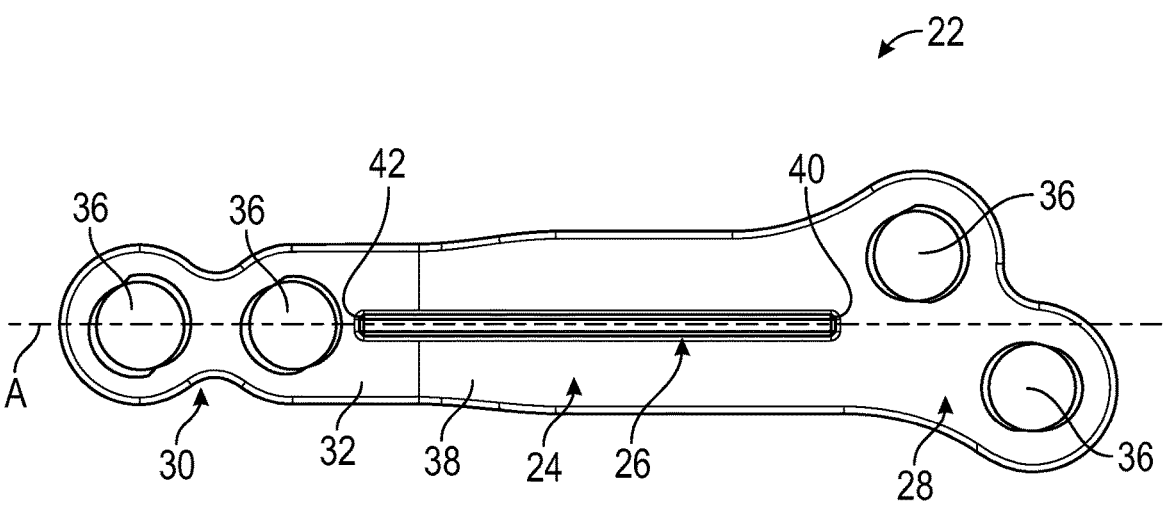
FIG. 4 is a bottom view of the internal beam plate of FIG. 2.
Figure 5:
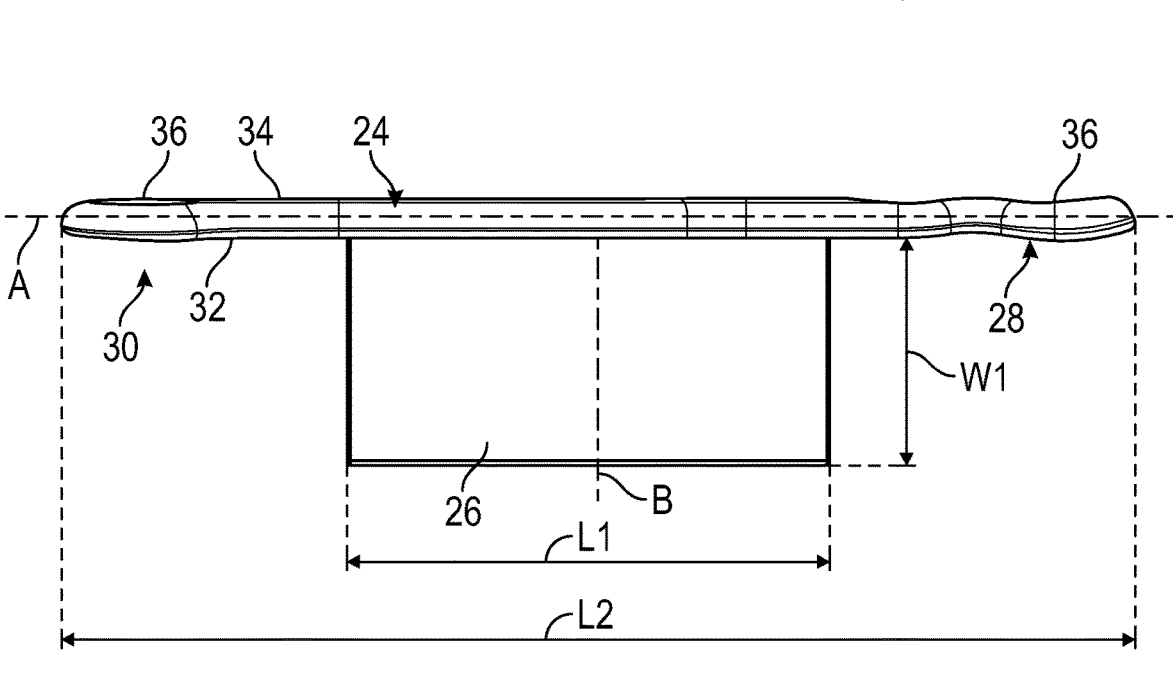
FIG. 5 is a side view of the internal beam plate of FIG. 2.

This disclosure is directed to internal beam plates and associated instrumentation for performing arthrodesis procedures, bone fracture procedures, osteotomy procedures, etc. Exemplary surgical methods that may be performed using the internal beam plates and associated instrumentation described herein include, but are not limited to, lapidus bunionectomy procedures, metatarsophalangeal (MTP) procedures, chevron procedures, fracture repair procedures, etc. The exemplary internal beam plates incorporate an integral beam that is configured to increase strength and stiffness across a fusion site. The exemplary cutting/prep guides are configured to allow surgeons to reduce, prepare, and cut bones for receiving the beam of the internal beam plate using one or more guides. These and other features of this disclosure are described in further detail below.

An exemplary internal beam plate may include a plate body and a beam. The plate body extends along a longitudinal axis between a first portion and a second portion and includes a bone contacting surface and an outer surface opposed to the bone contacting surface. The beam protrudes outwardly from the bone contacting surface.

In a further embodiment, a bone contacting surface of a plate body of an internal beam plate includes a curvature for conforming to a contour of a bone.

In a further embodiment, a plate body and a beam of an internal beam plate are integrated to establish a single-piece structure that excludes mechanical attachments for connecting the plate body and the beam together.

In a further embodiment, a beam of an internal beam plate protrudes away from a bone contacting surface of a plate body along a beam axis that is substantially perpendicular to a longitudinal centerline axis of the plate body.

In a further embodiment, a distance a beam of an internal beam plate protrudes from a bone contacting surface of a plate body is smaller than a first length of the beam and a second length of the plate body. The first length may be less than the second length.

In a further embodiment, a first set of openings is formed through a first portion of a plate body of an internal beam plate and a second set of openings are formed through a second portion of the plate body.

In a further embodiment, a first set of openings of a plate body are staggered along a longitudinal centerline axis and a second set of openings are aligned along the longitudinal centerline axis.

In a further embodiment, a first set of openings are disposed outboard of a first lengthwise end of a beam of an internal beam plate and a second set of openings are disposed outboard of a second lengthwise end of the beam.

An exemplary cutting/prep guide may include a guide body extending along a longitudinal centerline axis between a first section and a second section and including a bone contacting surface and an outer surface opposed to the bone contacting surface. A longitudinal cutting slot is formed through the guide body and extends along the longitudinal centerline axis. A vertical cutting slot is formed through the guide body and intersects the longitudinal cutting slot. A vertical guiding slot is formed through the guide body and extends in parallel with the vertical cutting slot but without intersecting the longitudinal cutting slot.

In a further embodiment, a guide body of a cutting/prep guide includes a mid-section that connects between a first section and a second section.

In a further embodiment, a longitudinal cutting slot of a cutting/prep guide extends across portions of a first section and a mid-section of a guide body, a vertical cutting slot is disposed within the mid-section, and a vertical guiding slot is disposed within a second section of the guide body.

In a further embodiment, a vertical cutting slot and a longitudinal cutting slot of a cutting/prep guide intersect one another within a mid-section of a guide body to form a cross or "+" shape.

In a further embodiment, a first section of a guide body of a cutting/prep guide includes a pair of spaced apart apertures, and the pair of spaced apart apertures flank an end portion of a longitudinal cutting slot. An additional aperture may be disposed adjacent to a second end portion of the longitudinal cutting slot.

An exemplary surgical method may include fixating a cutting/prep guide to a first bone, inserting a first K-wire through a vertical guiding slot of the cutting/prep guide and into a second bone, moving the first K-wire within the vertical guiding slot to re-position a second bone relative to the first bone, inserting a surgical cutting device through a longitudinal cutting slot of the cutting/prep guide or a second cutting/prep guide, preparing a slot within the first and second bones, removing the cutting/prep guide or the second cutting/prep guide, positioning a beam of an internal beam plate within the prepared slot, and fixating the internal beam plate to both the first bone and the second bone.

In a further embodiment, a first K-wire is moved to de-rotate a bone into a desired rotational position.

In a further embodiment, a bone is locked into position after being rotated to a desired rotational position. The bone may be locked by inserting a K-wire into the bone with the aid of a C-ring guide.

In a further embodiment, a slot depth is limited by the use of a cannulated depth stop that is adapted to receive a surgical cutting device.

In a further embodiment, a cutting/prep guide set for preparing a bone or bones for receiving an internal beam plate includes a first cutting/prep guide and a second cutting/prep guide.

FIG. 1 schematically illustrates select portions of a foot 10 of the human musculoskeletal system. A forefoot 12 of the foot 10 is specifically shown. The forefoot 12 includes multiples phalanges 14 (i.e., toes), multiples metatarsals 16 located proximal to the phalanges 14, and a trio of cuneiforms 18 (i.e., medial, middle, and lateral cuneiforms) located proximal to the metatarsals 16.

As illustrated, the foot 10 includes a bone abnormality 20. In an embodiment, the bone abnormality 20 is a hallux valgus abnormality (also referred to as a bunion abnormality) in which there is a medial deviation of a first metatarsal 16-1 and a lateral deviation of a first phalange 14-1. If not corrected, the bone abnormality 20 can lead to pain and arthritis.

Exemplary internal beam plates and associated instrumentation designed for repairing the bone abnormality 20 are detailed herein. Although the various teachings of this disclosure are detailed with reference to a bunion abnormality occurring at the first metatarsophalangeal (MTP) joint of the foot 10, the exemplary internal beam plates and instrumentation described herein may be used to repair other bone abnormalities, including fractures, of the foot, ankle, hand, wrist, etc.

FIGS. 2-6 illustrate an exemplary internal beam plate 22 for correcting bone abnormalities, such as the bone abnormality 20 of FIG. 1, for example. The internal beam plate 22 is a bone plate that may include a plate body 24 and a beam 26 that extends outwardly from the plate body 24. In an embodiment, the plate body 24 and the beam 26 are integrated to establish a single-piece structure. Stated another way, the internal beam plate 22 may be a monolithic bone plate without any mechanical attachments for connecting the plate body 24 and the beam 26 together. In an embodiment, the beam 26 is an integrally machined portion of the internal beam plate 22.

The plate body 24 extends along a longitudinal centerline axis A between a first or proximal portion 28 and a second or distal portion 30. The plate body 24 may include any size and shape. The plate body 24 may additionally include a bone contacting surface 32 and an outer surface 34 on an opposite side of the plate body 24 from the bone contacting surface 32. The bone contacting surface 32 may include a slight curvature for conforming to the contour of one or more bones.

The beam 26 may protrude outwardly from the bone contacting surface 32 in an opposite direction from the outer surface 34 of the plate body 24. The beam 26 may be tapered or non-tapered in a direction of a width W1 (see FIG. 5), may include angled or non-angled lengthwise ends 40, 42, and may protrude from a section 38 (best seen in FIG. 4) of the plate body 24 that connects between the first and second portions 28, 30. In an embodiment, the beam 26 protrudes away from the plate body 24 along a beam axis B that is substantially perpendicular to the longitudinal centerline axis A. As further discussed below, the beam 26 may be accommodated within one or more pre-formed bone slots for increasing the strength and rigidity across a fusion site.

Figure 6:
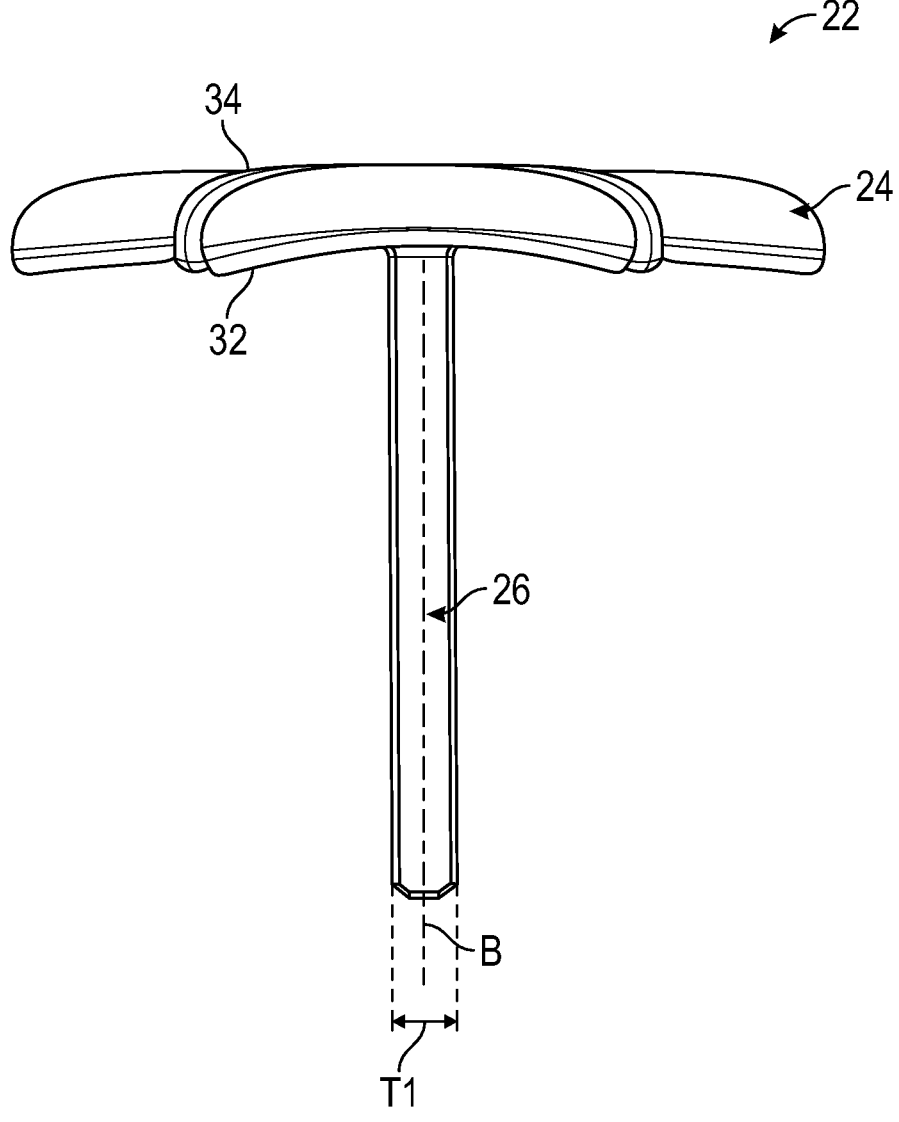
FIG. 6 is an end view of the internal beam plate of FIG. 2.

The beam 26 includes a length L1 (see FIG. 5), the width W1 (see FIG. 5), and a thickness T1 (see FIG. 6). In an embodiment, the length L1 of the beam 26 is shorter than a length L2 of the plate body 24. In some embodiments, the length L1 of the beam 26 is between about 25% and about 75% of the length L2 of the plate body 24. In other embodiments, the length L1 of the beam 26 is between about 40% and about 60% of the length L2 of the plate body 24. In this disclosure, the term "about" means that the expressed quantities or ranges need not be exact but may be approximated and/or larger or smaller, reflecting acceptable tolerances, conversion factors, measurement error, etc. The actual length of the beam 26 and the plate body 24 can vary depending on the fusion/fracture pattern, among other design criteria.

In another embodiment, the width W1, which is the distance the beam 26 extends away from the bone contacting surface 32, is smaller than the length L1 of the beam 26 and the length L2 of the plate body 24. In some embodiments, the width W1 of the beam 26 is between about 25% to about 50% of the length L1 of the beam 26. The actual width of the beam 26 can vary depending on the fusion/fracture pattern, among other design criteria.

The plate body 24 may include various openings 36 configured for receiving fixation devices (e.g. screws, etc., not shown in FIGS. 2-6) for fixating the internal beam plate 22 to one or more bones or bone segments. The openings 36 extend completely through the plate body 24 and therefore open through both the bone contacting surface 32 and the outer surface 34. In an embodiment, the first portion 28 and the second portion 30 of the plate body 24 each include a pair of openings 36. In an embodiment, the openings 36 of the first portion 28 are staggered along the longitudinal centerline axis A and the openings 36 of the second portion 30 are aligned along the longitudinal centerline axis A. However, other configurations are also contemplated, and thus the total number of openings 36 and their specific arrangement within the plate body 24 are not intended to limit this disclosure. The openings 36 of the first and second portions 28, 30, may be disposed outboard of opposing lengthwise ends 40, 42 of the beam 26 (see FIG. 4), in an embodiment.

The internal beam plate 22 may be made from any biocompatible material or combinations of biocompatible materials. Exemplary materials include, but are not limited to, titanium, titanium alloys, stainless steel, and thermoplastic materials.

In another embodiment, the internal beam plate 22 may optionally include features for achieving compression across a joint. For example, the internal beam plate 22 could include a gear-engaging mechanism (e.g., slot with integral teeth) for achieving compression across a joint.

Figures 7A, 7B, 7C:
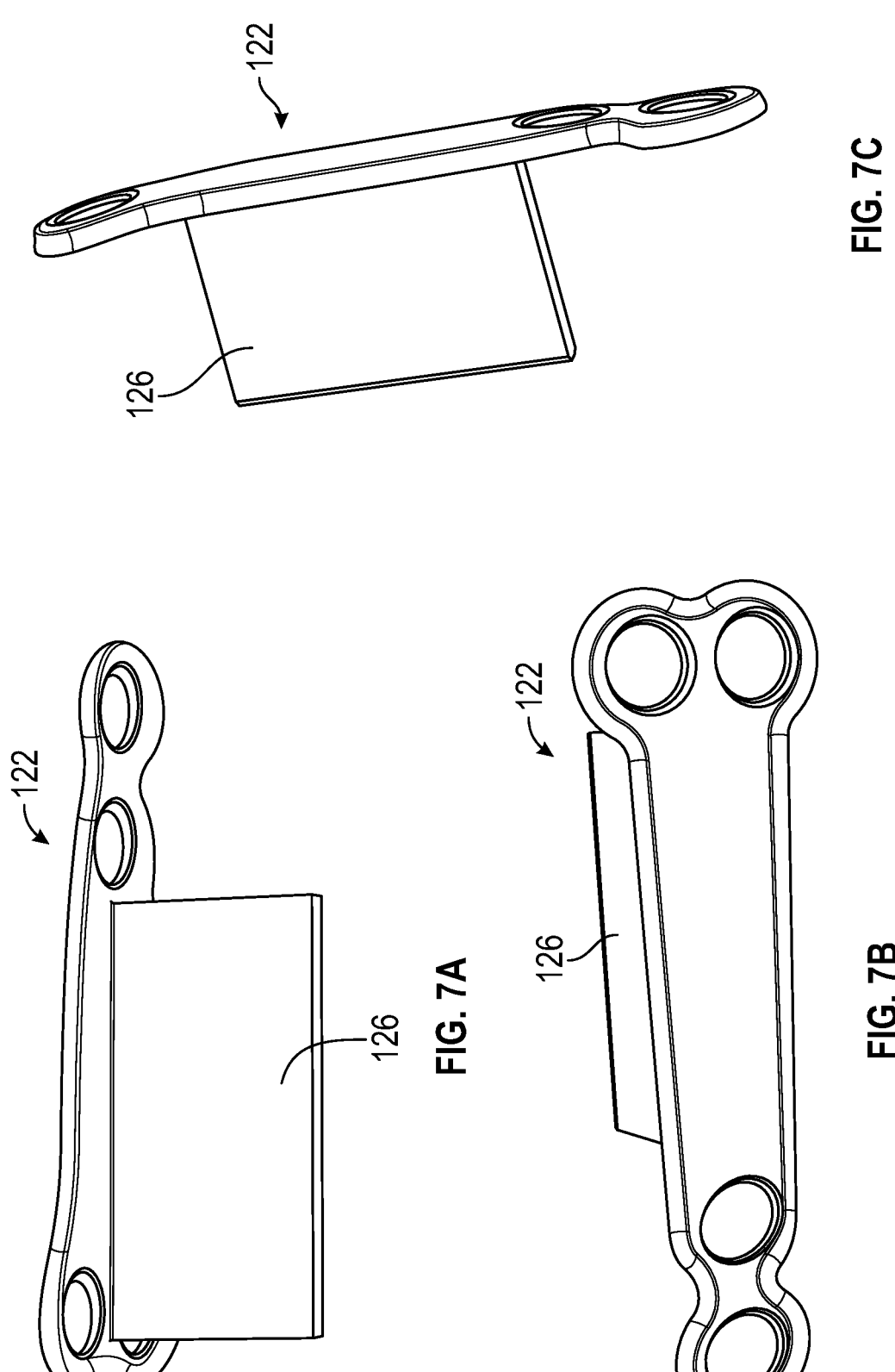
FIGS. 7A, 7B, and 7C illustrate another exemplary internal beam plate according to an embodiment of this disclosure.

FIGS. 7A, 7B, and 7C illustrate another exemplary internal beam plate 122. The internal beam plate 122 includes a slightly different shape than the internal beam plate 22 described above but is otherwise substantially similar to the internal beam plate 22. The internal beam plate 122 thus includes a beam 126 configured for increasing the strength and rigidity across a fusion site.

Figure 8:
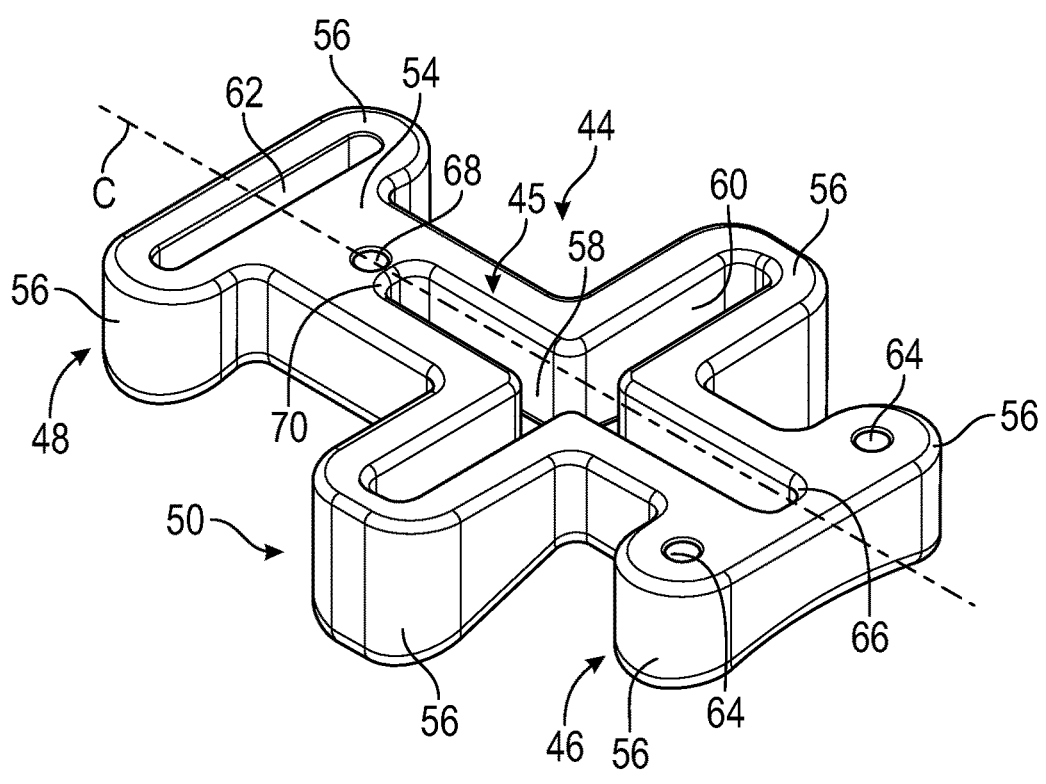
FIG. 8 is a perspective view of an exemplary cutting/prep guide for preparing a joint for receiving an internal beam plate according to an embodiment of this disclosure.
Figure 9:
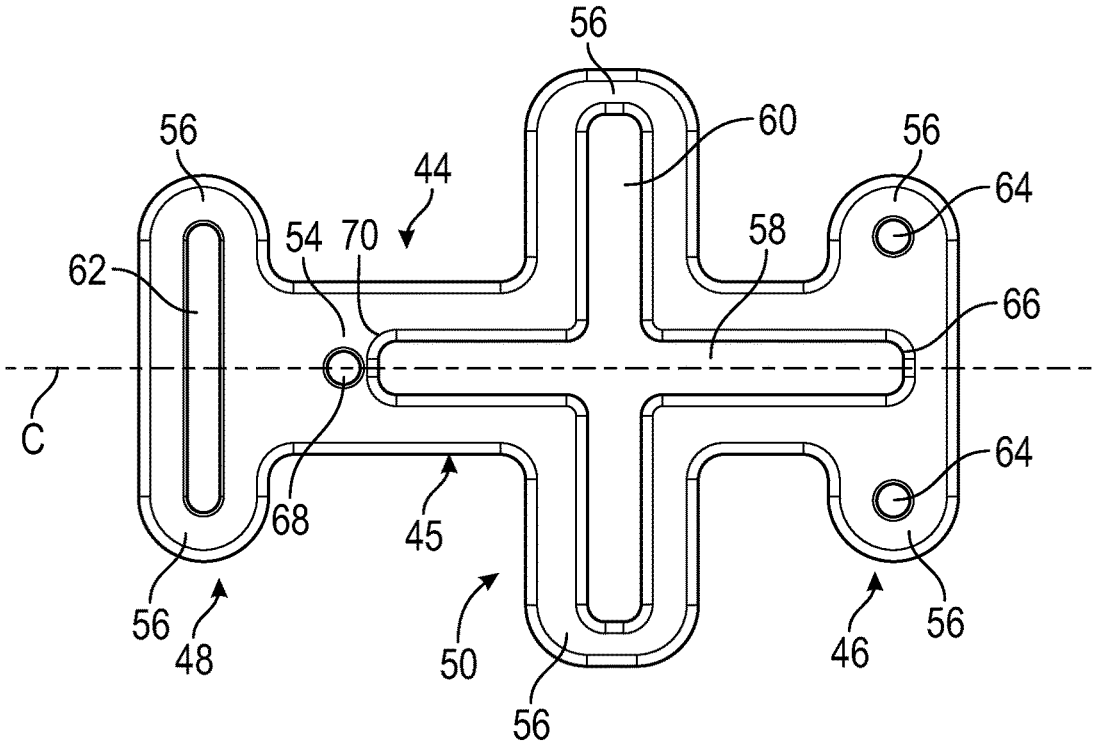
FIG. 9 is a top view of the cutting/prep guide of FIG. 8.
Figure 10:
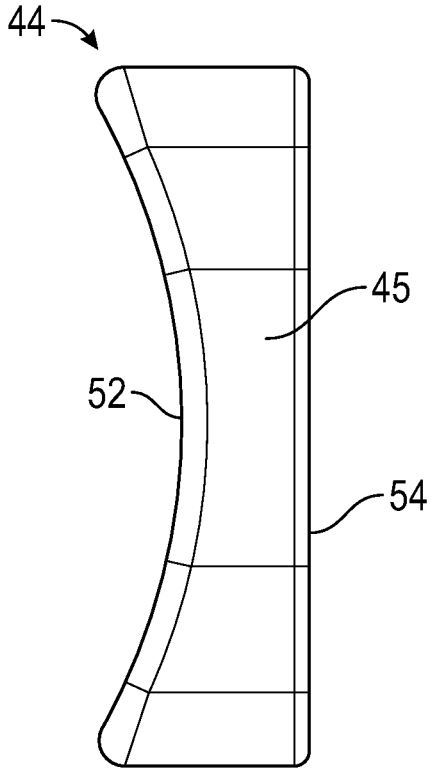
FIG. 10 is an end view of the cutting/prep guide of FIG. 8.

FIGS. 8-10 illustrate an exemplary cutting/prep guide 44 for preparing a bone or bones to receive the beams 26, 126 of the internal beam plates 22, 122 described above. The cutting/prep guide 44 includes a guide body 45 extending along a longitudinal centerline axis C between a first section 46 and a second section 48. A mid-section 50 connects between the first and second sections 46, 48. The cutting/prep guide 44 may additionally include a bone contacting surface 52 and an outer surface 54 on an opposite side of the cutting/prep guide 44 from the bone contacting surface 52. The bone contacting surface 52 may include a slight curvature for conforming to the contour of a bone or bones.

Each of the first section 46, the second section 48, and the mid-section 50 may include laterally extending feet 56. The feet 56 may extend laterally away from the cutting/prep guide 44 along axes that are transverse to the longitudinal centerline axis C. In an embodiment, the feet 56 of the mid-section 50 extend a greater distance laterally away from the cutting/prep guide 44 than the feet 56 of the first and second sections 46, 48.

A longitudinal cutting slot 58 may extend through portions of the first section 46 and the mid-section 50 of the cutting/prep guide 44. The longitudinal cutting slot 58 may extend in parallel with the longitudinal centerline axis C. In an embodiment, the longitudinal centerline axis C bisects the longitudinal cutting slot 58. The longitudinal cutting slot 58 is configured to guide a cutting tool for forming a slot in a bone or bones for receiving the beam 26, 126 of the internal beam plate 22, 122.

A vertical cutting slot 60 may intersect the longitudinal cutting slot 58 at about a perpendicular angle. In an embodiment, the vertical cutting slot 60 and the longitudinal cutting slot 58 intersect one another within the mid-section 50 to form a cross or "+" shape. The vertical cutting slot 60 is configured to guide a cutting tool for preparing a joint during a surgical procedure, such as for removing cartilage between adjacent bones of a joint, for example.

A vertical guiding slot 62 may be disposed within the second section 48 of the cutting/prep guide 44. The vertical guiding slot 62 extends in parallel with the vertical cutting slot 60 but does not intersect the longitudinal cutting slot 58. The vertical guiding slot 62 is configured to guide movement of a wire (e.g., a K-wire) or other surgical device for correcting the rotation of a bone during a surgical procedure.

The first section 46 of the cutting/prep guide 44 may additionally include a pair of spaced apart apertures 64. The apertures 64 may be disposed through the feet 56 of the first section 46 such that they at least partially flank an end portion 66 of the longitudinal cutting slot 58. The apertures 64 are configured for receiving K-wires or other surgical devices for temporarily securing the cutting/prep guide to a bone or bones.

An additional aperture 68 may be disposed through the cutting/prep guide 44 at a location that is slightly outboard of an opposite end portion 70 of the longitudinal cutting slot 58. The aperture 68 may be located in either the mid-section 50 or the second section 48 of the cutting/prep guide 44. The aperture 68 is configured for receiving a threaded K-wire for locking the rotation of a bone achieved via the vertical guiding slot 62 in place during a surgical procedure.

Each of the slots 58, 60, 62 and the apertures 64, 68 discussed above extend entirely through the thickness of the cutting/prep guide 44 (i.e., each opens through both the bone contacting surface 52 and the outer surface 54).

Figure 11:
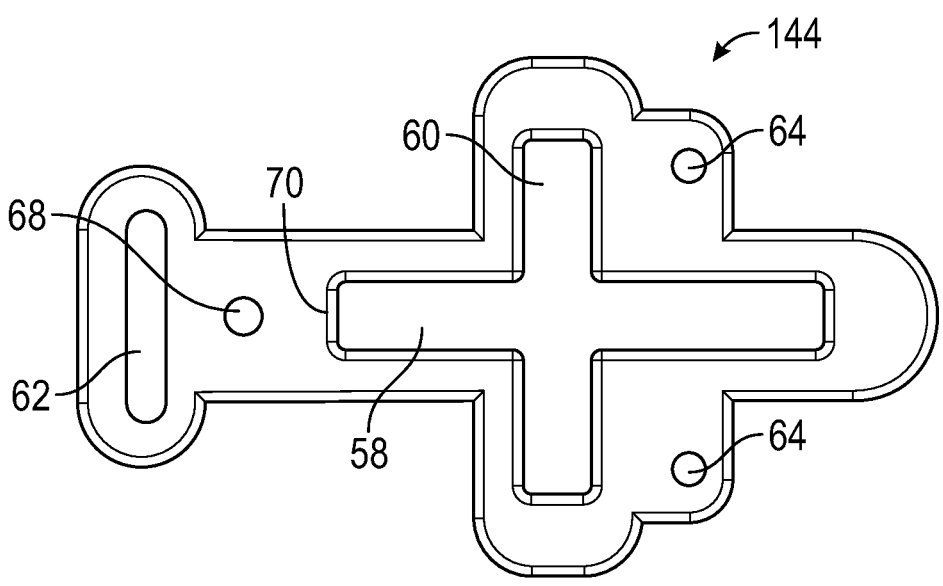
FIG. 11 illustrates an exemplary cutting/prep guide according to another embodiment of this disclosure.

FIG. 11 illustrates another exemplary cutting/prep guide 144. The cutting/prep guide 144 includes a slightly different shape and aperture placement than the cutting/prep guide 44 described above but is otherwise substantially similar to the cutting/prep guide 44. In this embodiment, the pair of apertures 64 are positioned slightly closer to the vertical cutting slot 60, and the aperture 68 is positioned further away from the end portion 70 of the of the longitudinal cutting slot 58 and thus closer to the vertical guiding slot 62. The specific placement of the apertures 64, 68 can vary depending on the fusion/fracture pattern, among other design criteria.

FIGS. 12-22, with continued reference to FIGS. 1-11, schematically illustrate, in sequential order, an exemplary surgical method for performing an arthrodesis procedure, such as a lapidus procedure for correcting a bunion abnormality of the first MTP joint of a foot, for example. Fewer or additional steps than are recited below could be performed within the scope of this disclosure. In addition, the recited order of steps depicted in FIGS. 12-22 is not intended to limit this disclosure.

Figure 12:
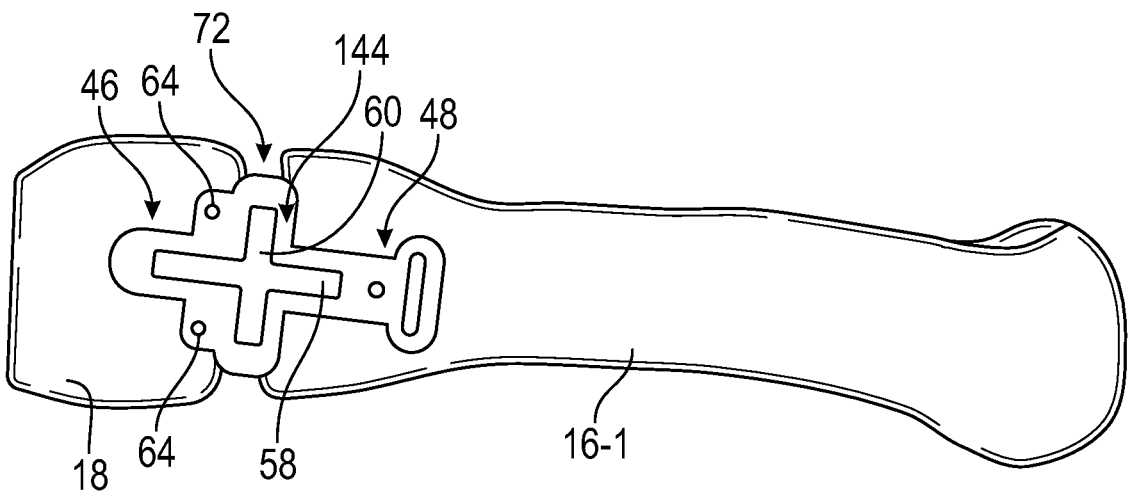
FIGS. 12, 13, 14, 15, 16, 17, 18, 19, 20, 21, and 22 schematically illustrate an exemplary surgical method for performing an arthrodesis procedure according to an embodiment of this disclosure.
Figure 13:
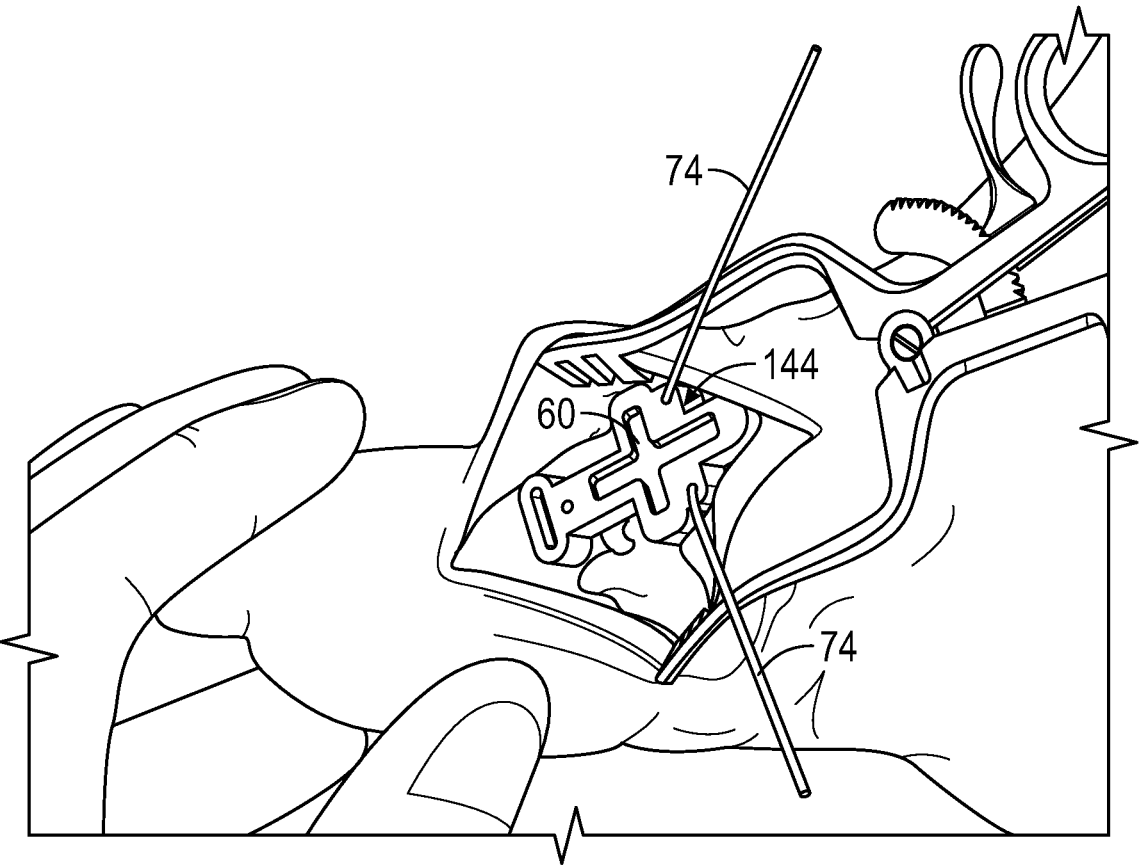

Referring first to FIGS. 12-13, the cutting/prep guide 144 (or 44) may be secured to a medial surface of cuneiform 18 associated with a first tarsometatarsal (TMT) joint 72 of the foot 10. For example, a K-wire 74 may be inserted through each of the apertures 64 of the cutting/prep guide 44 and then into the cuneiform 18 to temporarily fixate the cutting/ prep guide 44 in place relative to the TMT joint 72. In the fixated position, the first section 46 of the cutting/prep guide 44 faces proximally and the second section 48 faces distally. In an embodiment, the cutting/prep guide 44 is aligned such that the vertical cutting slot 60 is positioned over the cartilage of the distal surface of the cuneiform 18 and the proximal surface of the first metatarsal 16-1.

Figure 14:
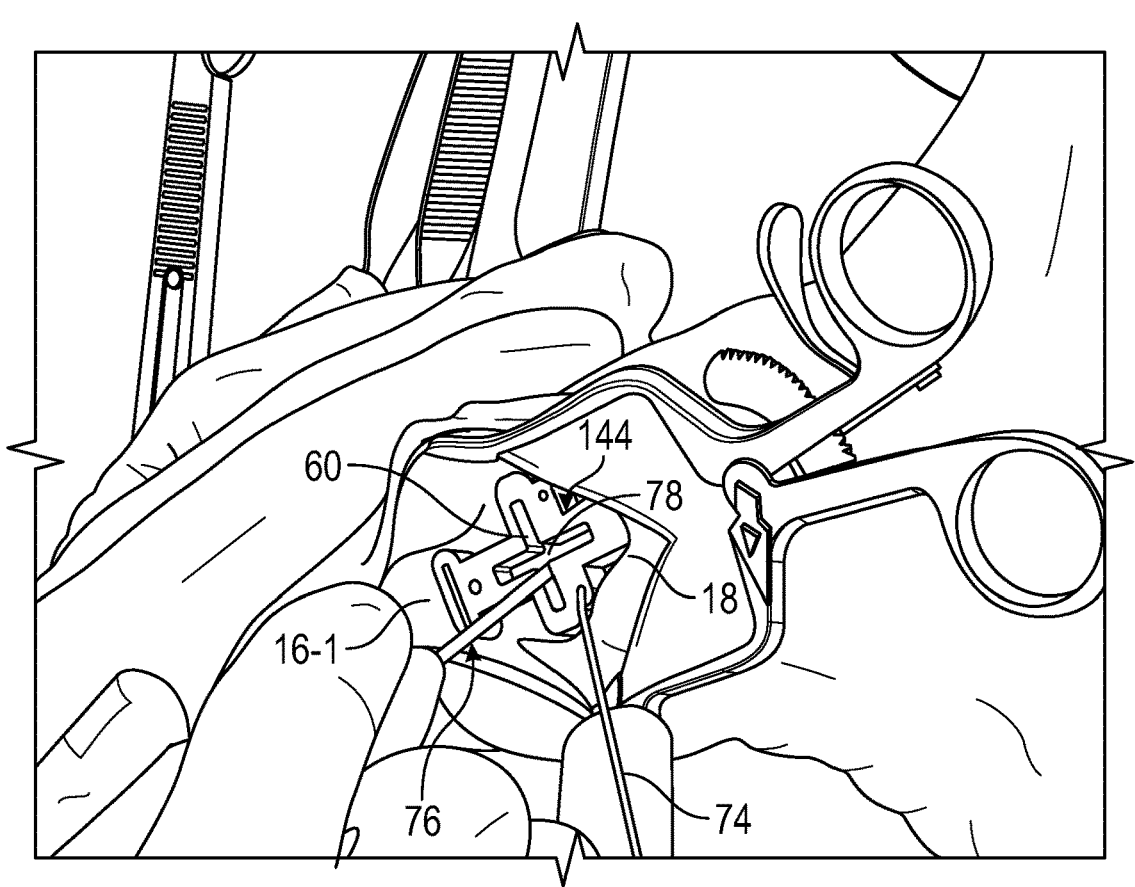
Figure 15:
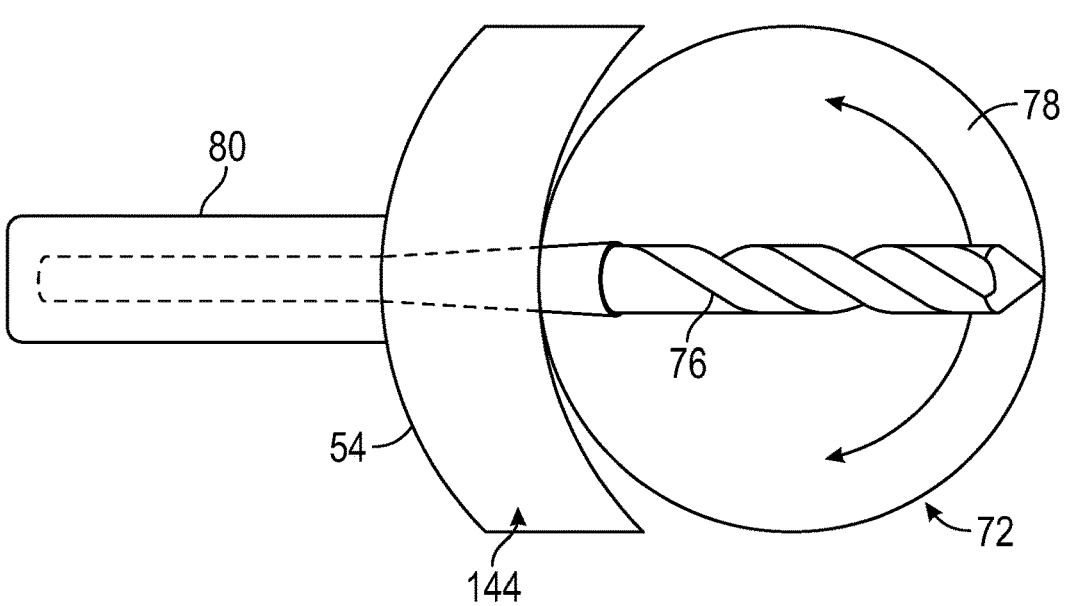

Next, as shown in FIG. 14, the cuneiform 18 and the first metatarsal 16-1 may be prepped for performing an arthrodesis using a surgical cutting device 76, such as a minimally invasive burr. For example, the surgical cutting device 76 may be inserted through the vertical cutting slot 60 in order to remove the cartilage 78 of the distal surface of the cuneiform 18 and the proximal surface of the first metatarsal 16-1. A cannulated depth stop 80 (see FIG. 15) may be placed over the surgical cutting device 76 prior to insertion through the vertical cutting slot 60 to prevent over-insertion of the surgical cutting device 76 into laterally adjacent joints. The cannulated depth stop 80 may abut against the outer surface 54 of the cutting/prep guide 144 to prevent the over-insertion.

Figure 16:
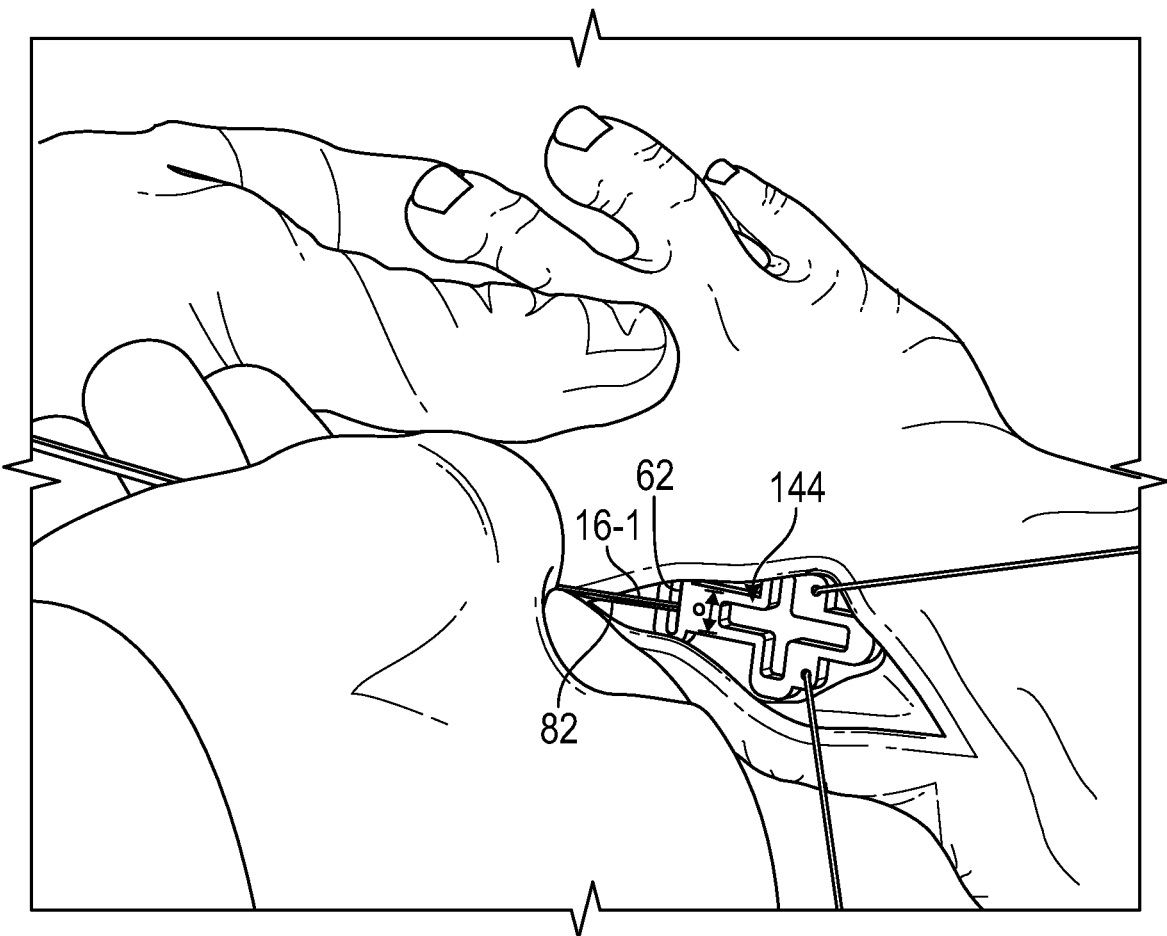

Referring next to FIGS. 16, a K-wire 82 may be inserted through the vertical guiding slot 62 and then into the first metatarsal 16-1. The K-wire 82 may be moved within the vertical guiding slot 62 for manipulating a positioning of the first metatarsal 16-1, such as for de-rotating the first metatarsal 16-1, for example.

Figure 17:
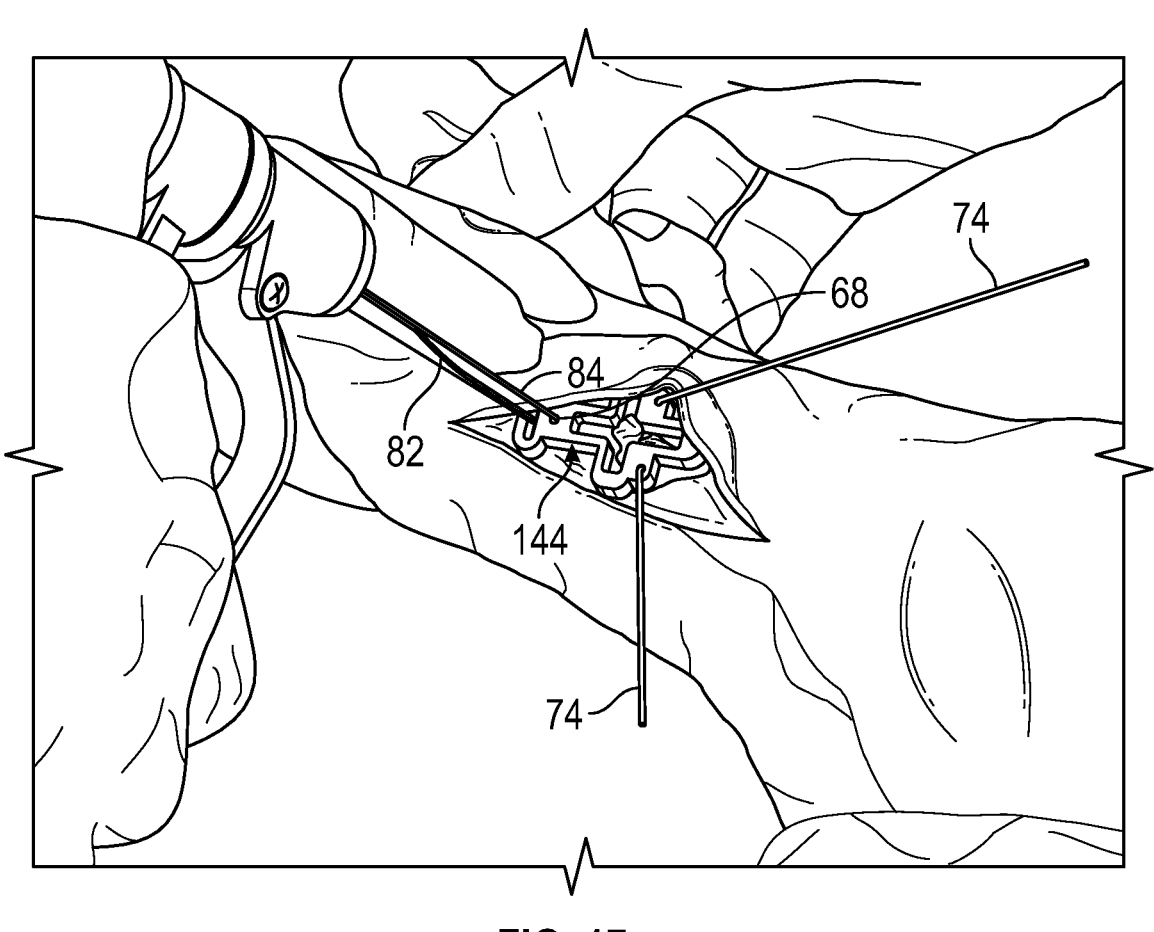
Figure 18:
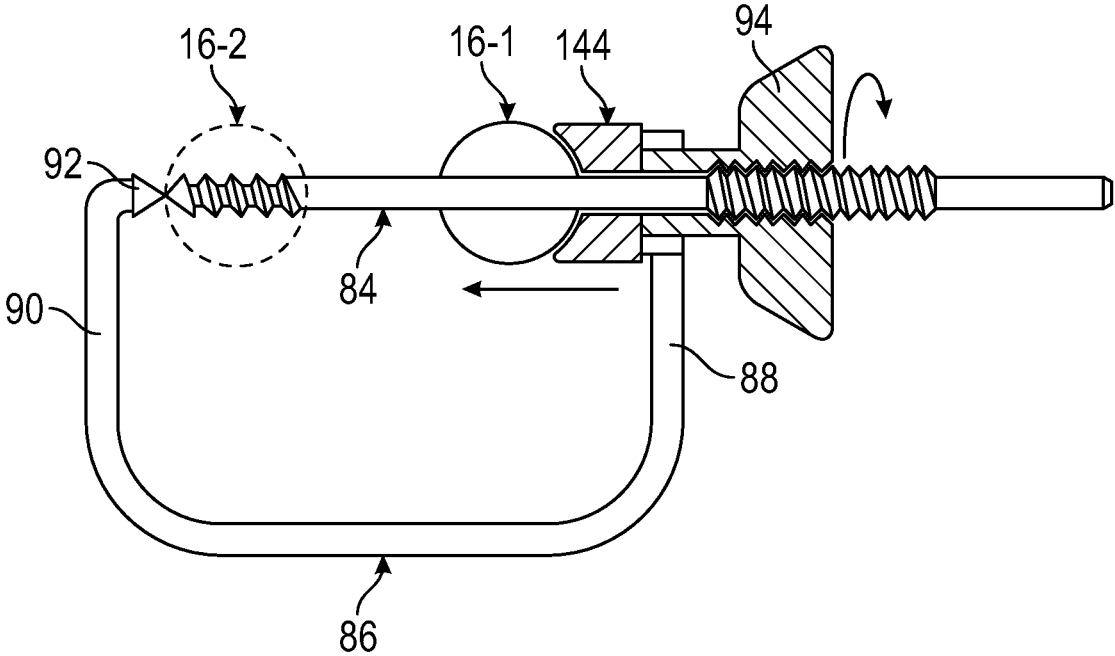

Once achieving a desired rotational position of the first metatarsal 16-1, the positioning of the first metatarsal 16-1 may be locked in place by inserting a threaded K-wire 84 through the aperture 68 of the cutting/prep guide 44 in the manner shown in FIGS. 17-18. The threaded K-wire 84 may extend through the first metatarsal 16-1 and a second metatarsal 16-2. A C-ring guide 86 may be used to properly position the threaded K-wire 84. The C-ring guide 86 may include a first clamp arm 88 for clamping the cutting/prep guide 144 to the first metatarsal 16-1 and a second clamp arm 90 for clamping to the second metatarsal 16-2. The second clamp arm 90 may include a pointed tip 92 for centering the insertion path of the threaded K-wire 84.

A threaded grommet 94 may be received over the threaded K-wire 84 at the medial side of the TMT joint 72. The threaded grommet 94 may be rotated to move the first metatarsal 16-1 in a direction toward the second metatarsal 16-2, thereby achieving a desired level of intramedullary reduction between these bones.

Figure 19:
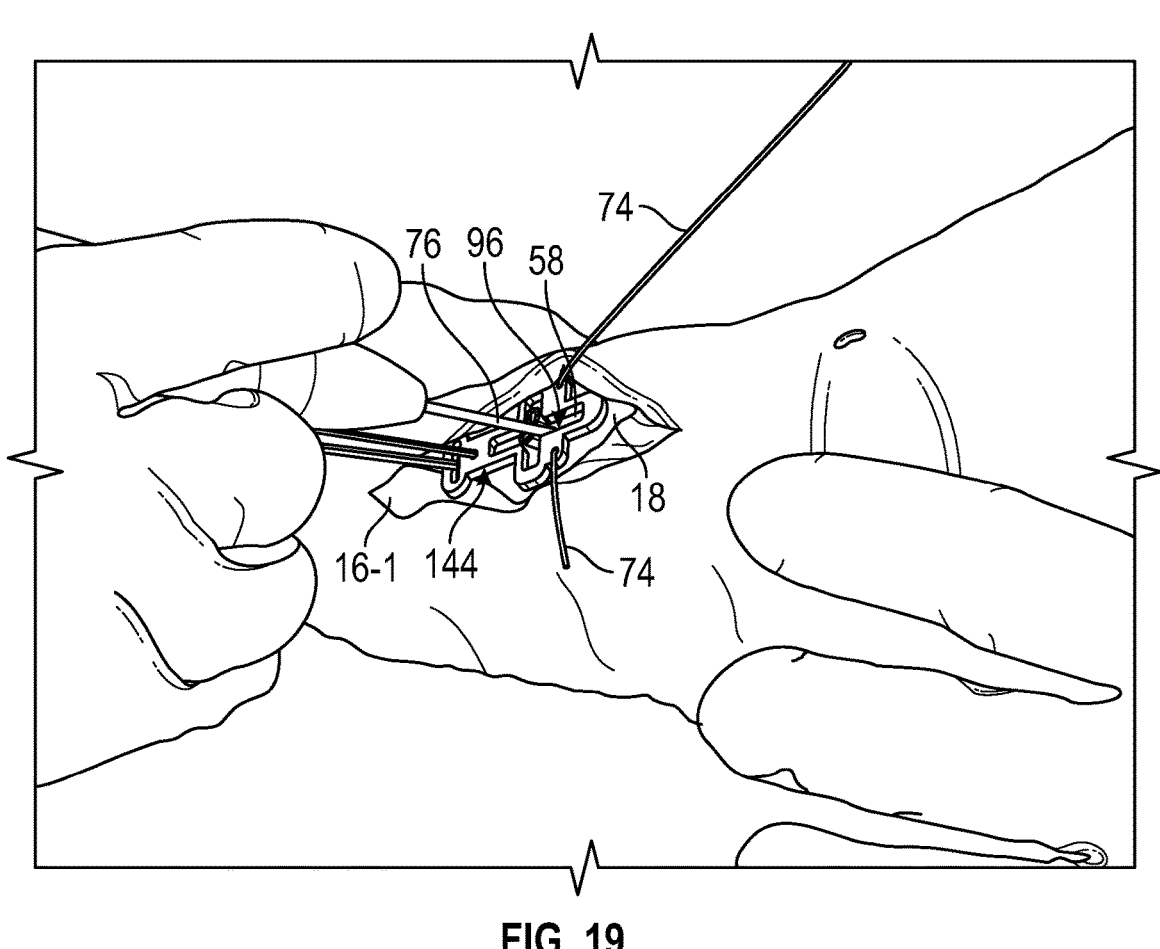
Figure 20:
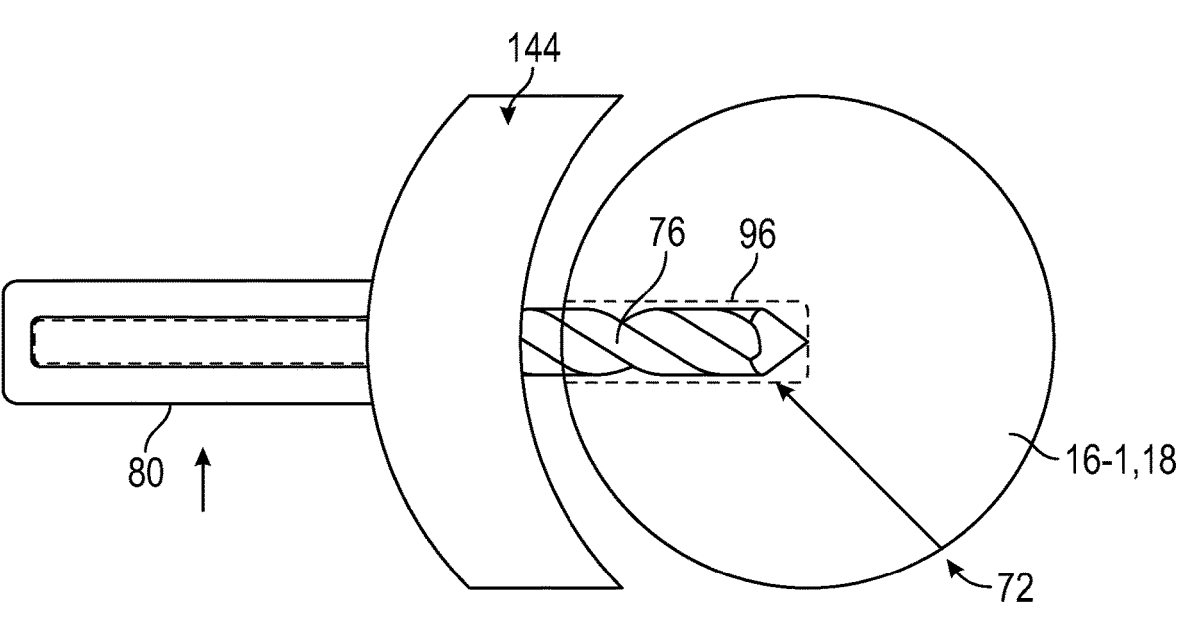

Referring now to FIG. 19, the reduced first metatarsal 16-1 and the cuneiform 18 may be further prepared for receiving the beam 26 of the internal beam plate 22. For example, the surgical cutting device 76 may be inserted through the longitudinal cutting slot 58 for forming a slot 96 into the first metatarsal 16-1 and the cuneiform 18. The slot 96 only extends partially through each of the first metatarsal 16-1 and the cuneiform 18 (i.e., only extends through first cortexes of the bones). The cannulated depth stop 80 may be used to limit the insertion depth of the surgical cutting device 76 (see FIG. 20), thereby preventing violation of the second cortexes. The slot 96 is sized and shaped to accommodate the beam 26 of the internal beam plate 22.

Figure 21:
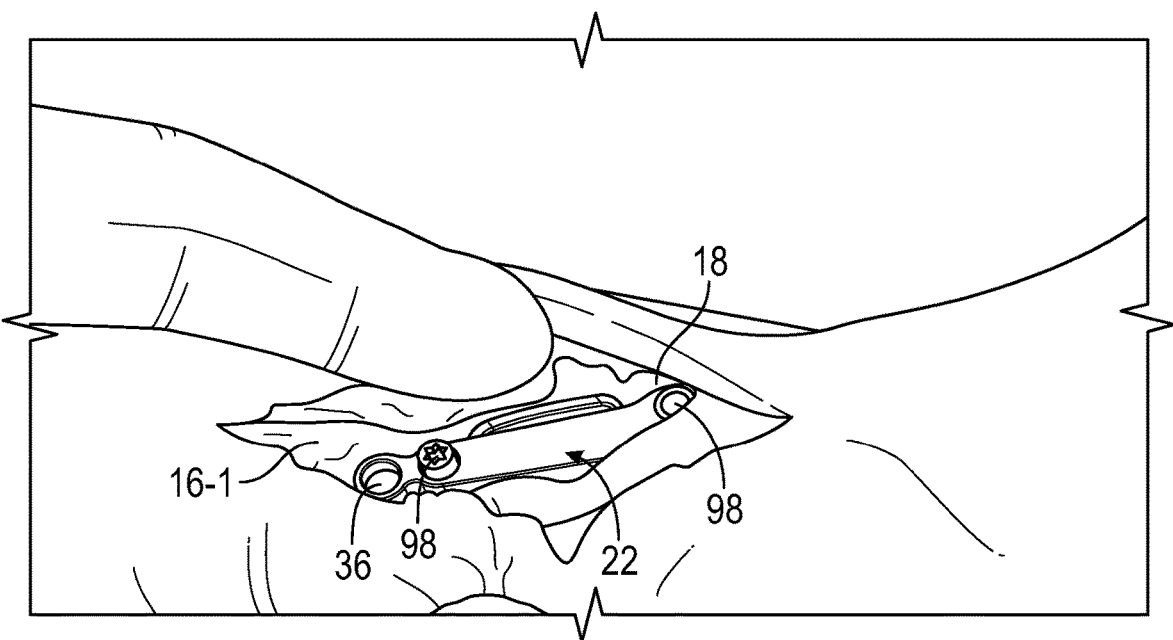
Figure 22:
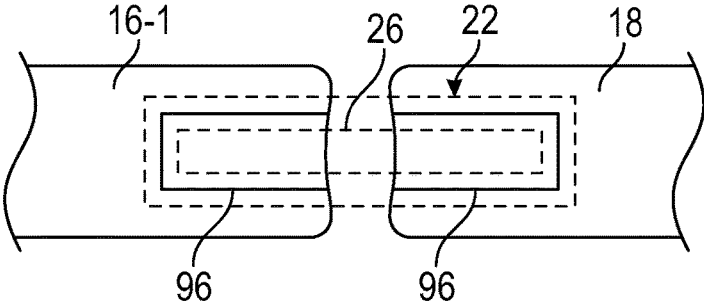

Next, as illustrated by FIG. 21, the cutting/prep guide 44 is removed and the internal beam plate 22 is positioned in place by inserting the beam 26 into the already prepared slot 96 (schematically shown in FIG. 22). The threaded grommet 94 (see FIG. 18) may optionally be rotated additionally to further compress and reduce the intramedullary angle between the first and second metatarsals 16-1, 16-2. Once the desired intramedullary reduction is achieved, fixation devices 98, such as screws, may be inserted into the openings 36 of the internal beam plate 22 to secure the internal beam plate to the first metatarsal 16-1 and the cuneiform 18. Providing the fusion at the TMT joint 72 allows for proper function at the MTP joint, thereby aiding to correct the bone abnormality 20.

Alternatively, once the IM reduction is achieved via the cutting/prep guide 44, 144, the surgeon can place a suture-button construct (e.g., a Mini-Tightrope construct) across the 1st metatarsal 16-1 and into the second metatarsal 16-2 to maintain the IM angle before removing the cutting/prep guide 44, 144. At that point, the surgeon can remove the cutting/prep guide 44, 144 and then position and fixate the internal beam plate 22 over the prepared bones.

The surgical devices described herein, including but not limited to the internal beam plates, the cutting/prep guides, the C-guide, the K-wires, etc., may collectively be referred to as a surgical system or as a surgical kit. The exemplary surgical systems provide an innovative way to add strength and stiffness across a fusion or fracture site via an integral beam of the internal beam plate.

Figure 23:
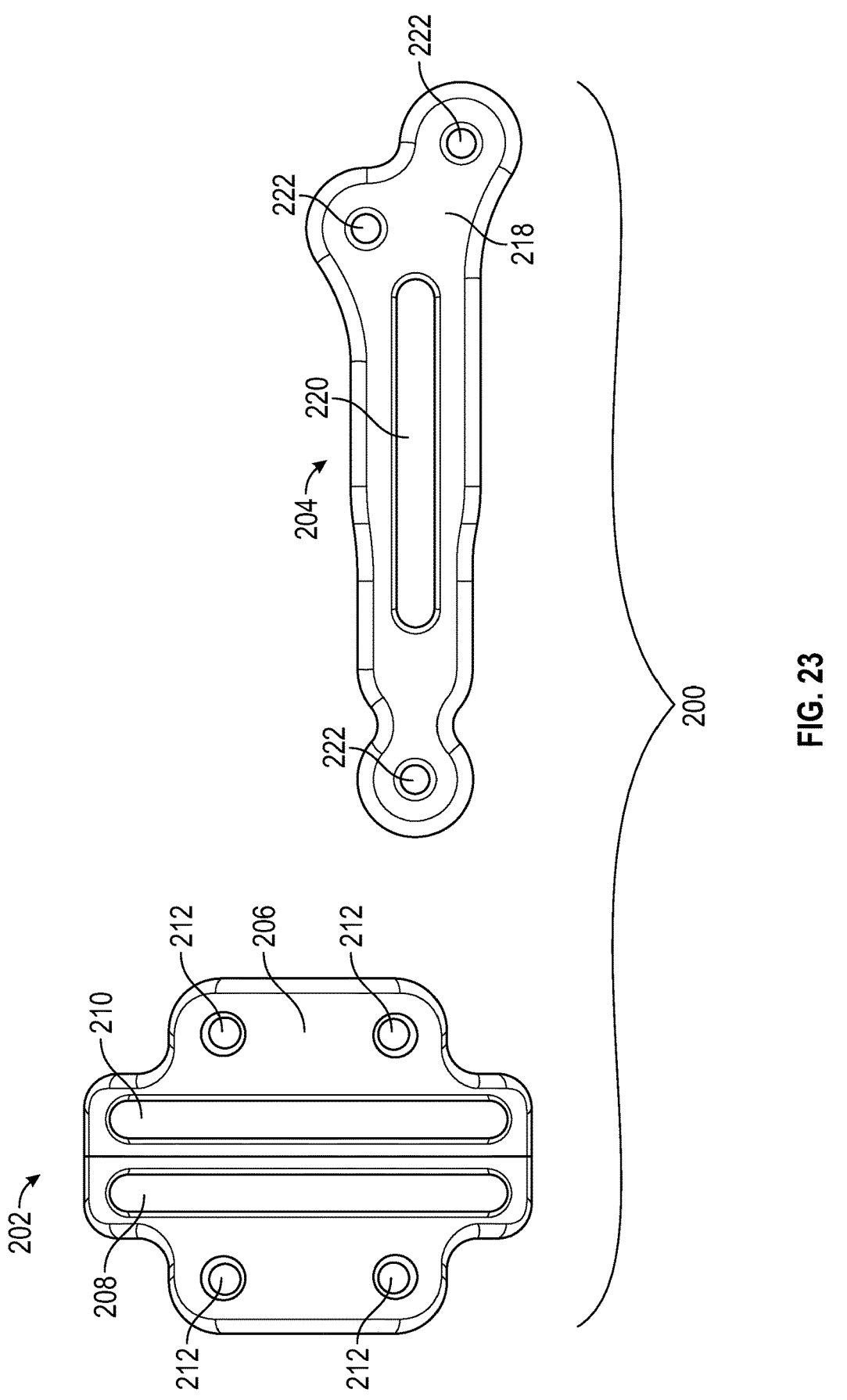
FIG. 23 is a top view of a cutting/prep guide set for preparing a joint for receiving an internal beam plate according to another embodiment of this disclosure.

In the above embodiments, a single cutting/prep guide is used to prepare one or more bones of a joint for receiving the beam of an internal beam plate. However, multiple cutting/ prep guides could alternatively be utilized. In this regard, FIGS. 23 and 24 illustrate a cutting/prep guide set 200 for preparing the bone(s) to receive the beam of any of the internal beam plates described herein.

The exemplary cutting/prep guide set 200 may include a first cutting/prep guide 202 and a second cutting/prep guide 204. In an embodiment, the first cutting/prep guide 202 is configured for preparing vertical or transverse cuts in a bone or bones, and the second cutting/prep guide 204 is configured for preparing longitudinal or sagittal cuts in the bone or bones. The vertical or transverse cuts prepare the joint by removing cartilage between adjacent bones, for example, and the longitudinal or sagittal cuts prepare the joint for receiving the beam of the internal beam plate.

The first cutting/prep guide 202 may include a guide body 206, a first vertical cutting slot 208, a second vertical cutting slot 210, and a plurality of apertures 212. The first vertical cutting slot 208 and the second cutting vertical cutting slot 210 are formed through the guide body 206 and are configured to guide a cutting tool for preparing a joint during a surgical procedure. For example, the first vertical cutting slot 208 may guide the cutting tool for removing cartilage associated with a first bone (e.g., a metatarsal bone), and the second vertical cutting slot 210 may guide the cutting tool for removing cartilage associated with a second bone (e.g., a cuneiform). The cartilage associated with each bone may therefore be prepped individually from that of the other bone. The apertures 212 are configured for receiving K-wires or other surgical devices for temporarily securing the first cutting/prep guide 202 to a bone or bones.

Figure 24:
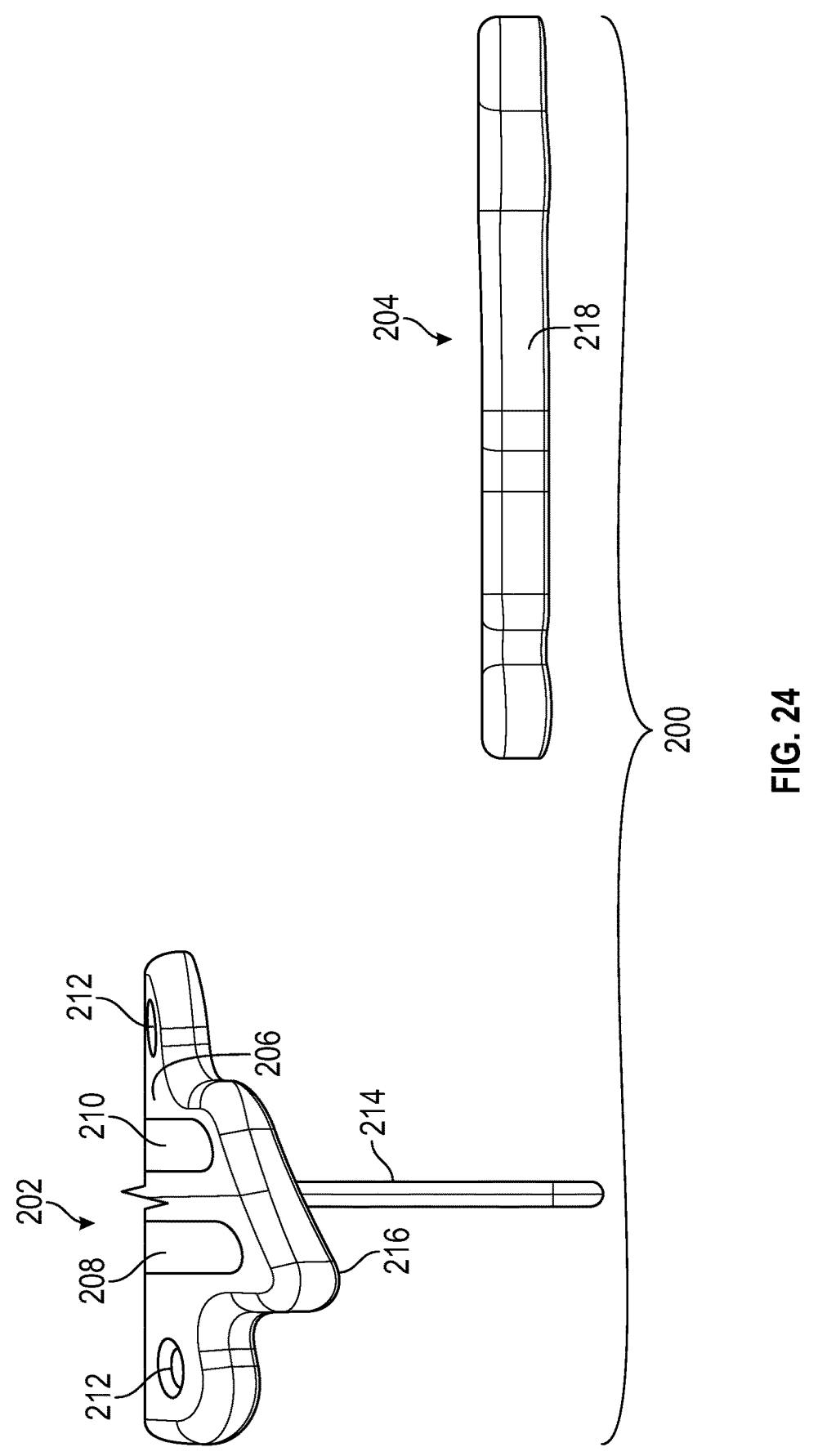
FIG. 24 is a side view of the cutting/prep guide set of FIG. 23.

The first cutting/prep guide 202 may additionally include a beam structure 214 (see FIG. 24). The beam structure 214 may protrude outwardly of a bone contacting surface 216 of the guide body 206. The beam structure 214 is configured to sit within the joint for positioning and stabilizing the first cutting/prep guide 202 for performing the vertical cuts.

The second cutting/prep guide 204 may include a guide body 218, a longitudinal cutting slot 220, and a plurality of apertures 222. The longitudinal cutting slot 220 is formed through the guide body 218 and is configured to guide a cutting tool for forming a slot in a bone or bones for receiving the beam of the internal beam plate. The apertures 222 are configured for receiving K-wires or other surgical devices for temporarily securing the second cutting/prep guide 204 to one or more bones.

The cutting/prep guide set 200 could be used in a surgical method similar to that described in FIGS. 12-22. When the cutting/prep guide set 200 is used, the first cutting/prep guide 202 may first be used to remove cartilage from the distal surface of the cuneiform and the proximal surface of the first metatarsal, and the second cutting/prep guide 204 may subsequently be used to prepare a bone slot for receiving the beam of the internal beam plate.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. An internal beam plate, comprising:
a plate body extending along a longitudinal centerline axis between a first portion and a second portion and including a bone contacting surface, an outer surface opposed to the bone contacting surface, and a peripheral side wall connecting between the bone contacting surface and the outer surface, wherein the first portion of the plate body protrudes outwardly at a first curved peak and a second curved peak, and the second portion of the plate body includes a single curved peak; and
a beam that protrudes outwardly from the bone contacting surface,
wherein the beam is non-tapered across a majority of a distance the beam protrudes from the bone contacting surface,
wherein the beam is the sole beam protruding from the bone contacting surface of the plate body of the internal beam plate,
wherein the beam includes a first length and the beam extends parallel to the longitudinal centerline axis of the plate body between a first lengthwise end and a second lengthwise end of the beam,
wherein the beam includes a width that is a distance the beam protrudes away from the bone contacting surface of the plate body,

wherein the beam includes a thickness measured between a first side of the beam and second side of the beam, wherein the first side and the second side of the beam are nearer to the longitudinal centerline axis of the plate body than to the peripheral side wall of the plate body, wherein the first length of the beam is larger than the thickness of the beam.

2. The internal beam plate as recited in claim 1, wherein the bone contacting surface includes a curvature for conforming to a contour of a bone.

3. The internal beam plate as recited in claim 1, wherein the plate body and the beam are integrated to establish a single-piece structure that excludes mechanical attachments for connecting the plate body and the beam together.

4. The internal beam plate as recited in claim 1, wherein the beam protrudes away from the bone contacting surface along a beam axis that is substantially perpendicular to the longitudinal centerline axis, and further wherein the distance the beam protrudes from the bone contacting surface is smaller than the first length of the beam and a second length of the plate body, and further wherein the first length is less than the second length.

5. The internal beam plate as recited in claim 1, comprising a first set of openings formed through the first portion of the plate body and a second set of openings formed through the second portion of the plate body, wherein the first length extends across a majority of a distance that spans between the first set of openings and the second set of openings, and further wherein the first set of openings are staggered along the longitudinal centerline axis and the second set of openings are aligned along the longitudinal centerline axis.

6. The internal beam plate as recited in claim 5, wherein the first set of openings are disposed outboard of the first lengthwise end of the beam and the second set of openings are disposed outboard of the second lengthwise end of the beam.

7. The internal beam plate as recited in claim 1, wherein the first length of the beam is less than a second length of the plate body.

8. The internal beam plate as recited in claim 7, wherein the first length is between about 25% and about 75% of the second length.

9. The internal beam plate as recited in claim 7, wherein the first length is between about 40% and about 60% of the second length.

10. The internal beam plate as recited in claim 7, wherein the distance the beam protrudes from the bone contacting surface is less than the first length of the beam.

11. The internal beam plate as recited in claim 10, wherein the distance the beam protrudes from the bone contacting surface is between about 25% and about 50% of the first length.

12. The internal beam plate as recited in claim 1, wherein the thickness of the beam is a uniform thickness.

13. The internal beam plate as recited in claim 1, wherein the first lengthwise end or the second lengthwise end is angled relative to the longitudinal centerline axis.

14. The internal beam plate as recited in claim 1, wherein the first curved peak of the first portion of the plate body is closer to the second portion of the plate body than the second curved peak of the first portion of the plate body.

15. The internal beam plate as recited in claim 14, wherein the longitudinal centerline axis intersects through the second curved peak of the first portion of the plate body and through the single curved peak of the second portion of the plate body.

16. The internal beam plate as recited in claim 15, wherein the longitudinal centerline axis intersects through a first opening formed through the single curved peak and a second opening of the second portion of the plate body but does not intersect through a third opening formed through the first curved peak or a fourth opening formed through the second curved peak.

\* \* \* \* \*